United States Patent
Hong et al.

(10) Patent No.: US 10,214,468 B1
(45) Date of Patent: Feb. 26, 2019

(54) METHOD FOR CO-PRODUCTION OF 1-CHLORO-3,3,3-TRIFLUOROPROPENE, 2,3,3,3-TETRAFLUOROPROPENE AND 1,3,3,3-TETRAFLUOROPROPENE

(71) Applicants: Zhejiang Quzhou Juxin Fluorine Chemical Co., Ltd., Zhejiang (CN); Zhejiang Quhua Fluor-Chemistry Co Ltd, Zhejiang (CN); Zhejiang Engineering Design Co., Ltd., Zhejiang (CN)

(72) Inventors: Jiangyong Hong, Zhejiang (CN); Aiguo Wang, Zhejiang (CN); Bo Yang, Zhejiang (CN); Yan Zhang, Zhejiang (CN); Guojun Yu, Zhejiang (CN); Yang Zhao, Zhejiang (CN); Hao Ouyang, Zhejiang (CN); Hao Pan, Zhejiang (CN)

(73) Assignees: Zhejiang Quzhou Juxin Fluorine Chemical Co., Ltd., Zhejiang (CN); Zhejiang Quhua Fluor-Chemistry Co Ltd, Zhejiang (CN); Zhejiang Engineering Design Co., Ltd., Zhejiang (CN)

(*) Notice: Subject to any disclaimer, the term of this patent is extended or adjusted under 35 U.S.C. 154(b) by 0 days.

(21) Appl. No.: 16/079,085

(22) PCT Filed: Mar. 8, 2017

(86) PCT No.: PCT/CN2017/000220
§ 371 (c)(1),
(2) Date: Aug. 22, 2018

(87) PCT Pub. No.: WO2018/036077
PCT Pub. Date: Mar. 1, 2018

(30) Foreign Application Priority Data

Aug. 25, 2016 (CN) .......................... 2016 1 0733880

(51) Int. Cl.
| | | |
|---|---|---|
| C07C 17/20 | (2006.01) | |
| C07C 17/25 | (2006.01) | |
| C07C 17/383 | (2006.01) | |
| C07C 21/18 | (2006.01) | |
| B01J 23/26 | (2006.01) | |
| C07C 21/04 | (2006.01) | |
| B01D 3/14 | (2006.01) | |

(52) U.S. Cl.
CPC .............. *C07C 17/20* (2013.01); *B01D 3/143* (2013.01); *B01J 23/26* (2013.01); *C07C 17/25* (2013.01); *C07C 17/383* (2013.01); *B01D 2257/2064* (2013.01); *B01D 2257/2066* (2013.01); *B01J 2208/00017* (2013.01); *B01J 2208/00557* (2013.01); *B01J 2523/22* (2013.01); *B01J 2523/27* (2013.01); *B01J 2523/33* (2013.01); *B01J 2523/67* (2013.01); *C07B 2200/09* (2013.01); *C07C 21/04* (2013.01); *C07C 21/18* (2013.01)

(58) Field of Classification Search
CPC ......... C07C 17/04; C07C 17/21; C07C 17/25; C07C 17/358; C07C 21/18; C07C 19/10; C07C 19/08; C07C 2523/26; C07C 2523/06; C07C 17/383; C07C 17/20
See application file for complete search history.

(56) References Cited

U.S. PATENT DOCUMENTS

2018/0208528 A1* 7/2018 Giddis ................... C07C 17/04

FOREIGN PATENT DOCUMENTS

| CN | 101597209 | 12/2009 |
|---|---|---|
| CN | 102686543 | 9/2012 |
| CN | 102918010 | 2/2013 |
| CN | 103180275 | 6/2013 |
| CN | 103189338 | 7/2013 |
| CN | 104069878 | 10/2014 |
| CN | 103172488 | 10/2015 |

OTHER PUBLICATIONS

"International Search Report (Form PCT/ISA/210)", dated Jun. 1, 2017, with English translation thereof, pp. 1-6.

* cited by examiner

*Primary Examiner* — Jafar F Parsa
(74) *Attorney, Agent, or Firm* — JCIPRNET

(57) ABSTRACT

This invention discloses a method for co-production of 1-chloro-3,3,3-trifluoropropene, 2,3,3,3-tetrafluoropropene and 1,3,3,3-tetrafluoropropene. This method includes inputting the mixed gases of hydrogen fluoride and 1,1,1,3,3-pentachloropropane together with 1,1,2,3-tetrachloropropene into a first reactor for a reaction to obtain a reaction product; directly inputting the reaction product into a second reactor to perform a reaction in the presence of a catalyst; separating hydrogen chloride from the obtained product; obtaining 1-chloro-3,3,3-trifluoropropene, 2,3,3,3-tetrafluoropropene and 1,3,3,3-tetrafluoropropene respectively after water washing, alkaline washing, drying and rectifying. This invention has the advantages of flexible production, simple process, small investment, low energy consumption and high conversion rate.

7 Claims, 1 Drawing Sheet

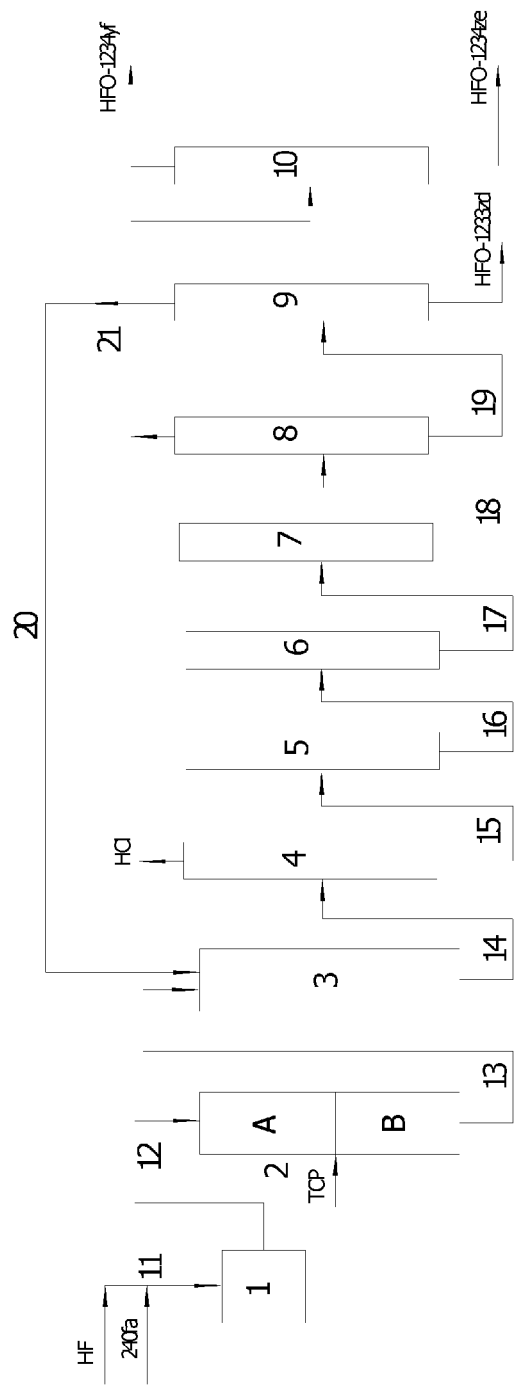

METHOD FOR CO-PRODUCTION OF 1-CHLORO-3,3,3-TRIFLUOROPROPENE, 2,3,3,3-TETRAFLUOROPROPENE AND 1,3,3,3-TETRAFLUOROPROPENE

CROSS-REFERENCE TO RELATED APPLICATION

This application is a 371 of international application of PCT application serial no. PCT/CN2017/000220, filed on Mar. 8, 2017, which claims the priority benefit of China application no. 201610733880.2, filed on Aug. 25, 2016. The entirety of each of the above-mentioned patent applications is hereby incorporated by reference herein and made a part of this specification.

BACKGROUND

1. Field of this Invention

This invention relates to a preparation method of alkenes containing fluorine and alkenes containing fluorine and chlorine, in particular to a method for co-production of 1-chloro-3,3,3-trifluoropropene, 2,3,3,3-tetrafluoropropene and 1,3,3,3-tetrafluoropropene.

2. DESCRIPTION OF RELATED ART

Hydrofluoroolefins (HFOs), such as 2,3,3,3-tetrafluoropropene (HFO-1234yf) and 1,3,3,3-tetrafluoropropene (HFO-1234ze), are important fourth-generation refrigerants and foamer. HFO-1234yf has a boiling point of −29.5° C., a GWP value of 4 and an atmospheric life of about 10 days. HFO-1234yf can serve as a refrigerant, an extinguisher, a propellant, a foamer, a foaming agent, a fluid carrier, a polishing abradant, and a dynamic circulating medium. A preferable prospected application of the HFO-1234yf is in the refrigerant field, as a fourth-generation refrigerant, replacing 1,1,1,2-tetrafluoroethane (HFC-134a). Two types of HFO-1234ze are available, namely Z type and E type. The Z-type has a boiling point of 9° C., and the E-type has a boiling point of −19° C. The GWP value is 6. The Z-type may serve as foamer, and the E type may be mixed with other substances to serve as a refrigerant.

HFO-1233zd, 1-chloro-,3,3,3-trifluoropropene, is abbreviated as LBA, has a boiling point of 19° C., an atmospheric life of 26 days, an ODP value of approximately zero, and a GWP value of <5, and is the first choice of a new-generation of environmentally-friendly foamer. HFO-1233zd is applicable to foaming polyurethane heat-insulating materials in fields such as household appliances, building insulation, cold-chain transmission and industrial insulation, and is the optimal foamer for replacing CFC, HCFC, HFC and other non-fluorocarbon foamer. Compared with the existing foamer systems (HFC-245fa and cyclopentane), HFO-1233zd has higher performance in the aspects of heat conductivity coefficient and overall energy consumption level. In comparison with the same type refrigerators using HFC-245fa and cyclopentane system, the heat conductivity coefficient of HFO-1233zd is reduced by 7% (in comparison with the HFC-245fa system) and by 12% (in comparison with the cyclopentane system), and the overall energy consumption is reduced by 3% (in comparison with HFC-245fa) and 7% (in comparison with cyclopentane).

HFO-1234yf can be prepared by three methods with industrial prospects, namely the 3,3,3-trifluoropropene method, hexafluoropropylene method, and 1,1,2,3-tetrachloropropene (TCP) method. The 3,3,3-trifluoropropene method has a long line, lots of waste water, waste gas and waste solids, and high product cost; the 1,1,2,3-tetrachloropropene method features fewer reaction steps and a high utilization rate of raw materials; and the hexafluoropropylene method has a long preparation line and a low total yield. Other preparation processes are all derived from the intermediate materials of the above mentioned three methods.

Two HFO-1234ze preparation methods with the industrial prospects include a 1,1,1,3,3-perfluoropropane (HFC-245fa) gas-phase HF-elimination method and a 1-chloro-3,3,3-trifluoropropene HF-addition method.

For example, Chinese Patent Publication No. CN201180052804A, published on Jul. 3, 2013 and titled with "Integrated Method for Co-production of Trans-1-Chloro-3,3,3-Trifluoropropene, Trans-1,3,3,3-Tetrafluoropropene, and 1,1,1,3,3-Perfluoropropane," disclosed an integrated method for co-production of (E) 1-chloro-3,3,3-trifluoropropene, (E) 1,3,3,3-tetrafluoropropene and 1,1,1,3,3-pentafluoropropane using a single chlorinated hydrocarbon raw material, namely 1,1,1,3,3-pentachloropropane (HCC-240fa). The method includes a combined liquid phase or gas phase reaction/purification operation for directly producing (E) 1-chloro-3,3,3-trifluoropropene (1233zd(E)). In a second liquid-phase fluorination reactor, 1233zd(E) and hydrogen fluoride (HF) contact each other under the presence of a catalyst to perform a reaction with a high conversion rate and high selectivity to generate 1,1,1,3,3-perfluoropropane (HCC-240fa). The third reactor is used to remove the hydrogen fluoride from the HFC-245fa through contacting a high alkaline solution in a liquid phase or using a dehydrofluorination catalyst in a gas phase to generate (E)1,3,3,3-tetrafluoropropene (1234ze(E)). After this operation, one or more extraction processes may be carried out to recover the 1234ze(E) product. The defects are found in the liquid-phase fluorination and liquid-phase dehydrofluorination processes, including a short reaction catalyst life, a lot of process waste liquid and high environmentally-friendly processing cost.

For example, Chinese Patent Publication No. CN201180027570A, published on Feb. 25, 2015 and titled with "Comprehensive Method for Co-production of Trans-1-Chloro-3,3,3-Trifluoropropene and Trans-1,3,3,3-Tetrafluoropropene," disclosed a comprehensive manufacturing method in combination with liquid-phase reactions and purification operations. According to the disclosed method, the trans-1-chloro-3,3,3-trifluoropropene and 3-chloro-1,1,1,3-tetrafluoropropene, which are precursors for manufacturing trans-1,3,3,3-tetrafluoropropene, are produced directly. Mixtures of co-products are easily separated through conventional distillation, and then hydrogen chloride is eliminated from the 3-chloro-1,1,1,3-tetrafluoropropene through contacting a high alkaline solution in a liquid phase or using a dehydrofluorination catalyst in a gas phase to produce the trans-1,3,3,3-tetrafluoropropene. The defects are found in the liquid-phase fluorination and liquid-phase dehydrofluorination processes, including a short reaction catalyst life, a lot of process waste liquid and high environmentally-friendly processing cost.

For example, Chinese Patent Publication No. CN102686543A, published on Sep. 19, 2012 and titled with "Gas Fluorination of 1230xa to 1234yf," relates to a method for preparation of 2,3,3,3-tetrafluoropropene (HFO-1234yf), including (1) allowing 1,1,2,3-tetrachloropropene (TC) to contact hydrogen fluoride in a gas phase with the existence of a fluorination catalyst; (2) separating the reaction mixture to obtain 2-chloro-3,3,3-trifluoropropene (HCFO-1233 xf)

and 1,1,1,2,2-pentafluoropropane (HFC-245cb), and inputting HCFO-1233xf and HFC-245cb into a reactor to generate HFO-1234yf. The defect is that some HFC-245cb is generated during the process. During the reaction process, a problem of balancing with HFO-1234yf occurred. Within the catalyst system, HCFO-1233xf and HFC-245cb cannot generate HFO-1234yf at the same time, and HFO-1234yf is synthesized through two-step reaction.

For example, Chinese Patent Publication No. CN101597209A, published on Sep. 9, 2009 and titled with "Integrated Method for Preparation of 2,3,3,3-Tetrafluoropropene" provides an integrated method for preparing 2,3,3,3-tetrafluoropropene. The method includes: reacting 1,1,2,3-tetrachloropropene and a first fluorinated reagent to generate 2-chloro-3,3,3-trifluoropropene (HCFO-1233xf) and a first intermediate composition of a first chlorine-containing side product; reacting the first intermediate composition of the first chlorine-containing side product and a second fluorinated reagent to generate 2-chloro-1,1,2,2-tetrachloropropene (HCFC-244bb) and a second intermediate composition of a second chlorine-containing side product; catalyzing at least part of the HCFC-244bb and eliminating the hydrogen chloride to generate 2,3,3,3-tetrafluoropropene. This process synthesizes the 2,3,3,3-tetrafluoropropene using three steps. HCFO-1233xf is converted into HCFC-244bb in a liquid-phase reactor. The catalyst is antimony halide. The reactor adopts TFE or PFA as the inner lining. The defect is that the reactor is seriously corroded inside and bulged. It is difficult to select equipment. The third step, namely saponification, generates a huge amount of waste water, waste gas and waste solids, and has a low yield.

SUMMARY

Aiming at defects in the prior arts, this invention provides a method for co-production of 1-chloro-3,3,3-trifluoropropene, 2,3,3,3-tetrafluoropropene and 1,3,3,3-tetrafluoropropene. This method is simple in process, low in investment, low in energy consumption and high in catalyst conversion rate.

In order to solve the above technical problems, this invention adopts the following technical solution: a method for co-production of 1-chloro-3,3,3-,trifluoropropene, 2,3,3,3-,tetrafluoropropene and, 3,3,3-,tetrafluoropropene includes the following steps:

(a) Hydrogen fluoride and 1,1,1,3,3-pentachloropropane (HCC-240fa) are preheated and then directed into a first reactor in a molar ratio of 9-15:1. The first reactor includes two sections, namely an upper section and a lower section. The upper section is filled with an aluminum oxide supported chromium metal catalyst, and the lower section is filled with a chromic oxide supported indium metal catalyst. The hydrogen fluoride and the 1,1,1,3,3-pentachloropropane are reacted in the upper section of the first reactor at a temperature of 200-400° C. and at an air flow rate of 300-1,000h$^{-1}$. The reaction product thereof enters the lower section of the first reactor to continuously react with the 1,1,2,3-tetrachloropropane, and the molar ratio of the 1,1,2,3-tetrachloropropane to the hydrogen fluoride is 3-5:9. A reaction product of the first reactor is obtained.

(b) The reaction product of the first reactor obtained in step (a) is directly directed into a second reactor, and the reaction product of the first reactor catalyzed by a catalyst of the second reactor at a temperature of 250-450° C. and at an air flow rate of 500-1,500 h$^{-1}$. A reaction product of the second reactor is obtained.

(c) The reaction product of the second reactor obtained in step (b) is directed into a hydrogen chloride tower to perform separation to obtain a tower bottom fraction and an tower top fraction of the hydrogen chloride tower. The tower top fraction is hydrogen chloride. The hydrogen chloride is refined to obtain hydrochloric acid;

(d) The tower bottom fraction of the hydrogen chloride tower is sequentially passed through a water washing tower, an alkaline washing tower and a drying tower to remove hydrogen fluoride and hydrogen chloride, and then enter a first rectifying tower to perform rectification. A tower bottom fraction and a tower top fraction of the first rectifying tower are obtained.

(e) The tower bottom fraction of the first rectifying tower is directed into a second rectifying tower for separation to obtain a product of 1-chloro-3,3,3-trifluoropropene and a tower top fraction of the second rectifying tower. The tower top fraction of the first rectifying tower is direct into a third rectifying tower for separation to obtain a product of 2,3,3,3-tetrafluoropropene at the top of the third rectifying tower and a 1,3,3,3-tetrafluoropropene product at the bottom of the third rectifying tower.

As a preferable embodiment of this invention, the tower top fraction of the second rectifying tower obtained in step (e) may be circulated to reenter the second reactor.

As a preferable embodiment of this invention, in step (a), the molar ratio of the hydrogen fluoride to the 1,1,1,3,3-pentachloropropane is preferably 9-12:1; the reaction temperature is preferably 250-320° C. and the air flow rate is preferably 500-800h$^{-1}$.

As a preferable embodiment of this invention, in step (b), the reaction temperature is preferably 300-400° C., and the air flow rate is preferably 800-1,200h$^{-1}$.

As a preferable embodiment of this invention, in step (a), the loading amount of chromium in the aluminum oxide supported chromium metal catalyst is 5-15 wt % (wt %, weight percentage content).

As a preferable embodiment of this invention, in step (a), the loading amount of indium in the chromic oxide supported indium metal catalyst is 3-10 wt %.

As a preferable embodiment of this invention, in step (b), the catalyst in the second reactor comprises the following ingredients in mass percentage: 70-80% of chromium oxide, 10-15% of magnesium oxide, and 5-15% of zinc oxide.

In this invention, the first reactor is divided into two sections, an upper section and a lower section. The upper section is filled with hydrogen fluoride and 1,1,1,3,3-pentachloropropane from the top, and the lower section is filled with 1,1,2,3-tetrachloropropene. Since the reaction of 1,1,2,3-tetrachloropropene and the HF is a strong exothermic reaction, so that the reacting materials in the upper section may carry heat away, without affecting the conversion rate of the 1,1,2,3-tetrachloropropene. The reaction temperature has a large influence on the activity of the catalyst and the selectivity of products. The increased reaction temperature helps to enhance the activity of the catalyst. Proper control over the reaction temperature may allow the conversion rate of the 1,1,1,3,3-pentachloropropane and the 1,1,2,3-tetrachloropropene to reach 100%. Therefore, the temperature of the upper section of the first reactor of this invention is selected to be 200-400° C., preferably 250-320° C., and the needed temperature of the lower section of the first reactor depends on the heat of the materials in the upper section brought into.

A fluorine-chlorine exchange reaction and an addition reaction of alkenes occur in the first reactor. The catalyst in the upper section of the first reactor is aluminum oxide supported chromium metal, and the catalyst in the lower section is chromic oxide supported indium metal. The catalyst in the upper section uses aluminum oxide as the support, and is capable of preventing quick reduction of the specific area of the catalyst due to strong heat release during reaction between the hydrogen fluoride and the 1,1,1,3,3-pentachloropropane, and the addition of chromium increases the activity of the catalyst. The catalyst in the lower section uses chromic oxide as the support to load indium metal, further enhancing the activity of the catalyst, and ensuring that the 1,1,1,3,3-pentachloropropane and the 1,1,2,3-tetrachloropropene may be completely converted under proper temperature conditions.

The molar ratio has a relatively large influence on the reaction. The HF required by the reactions in the upper and lower sections of the first reactor is imported from the upper section. Theoretically, 5 moles of HF are needed for the reaction of each mole of the 1,1,1,3,3-pentachloropropane in the upper section, and 3-4 moles of HF are needed for the reaction of each mole of the 1,1,2,3-tetrachloropropene in the lower section. A huge amount of HF in the upper section can carry heat away, and the reaction heat in the lower section is supplied by and brought away by the upper section, and comprehensive utilization of the heat and reducing energy consumption is thus realized. However, excessive HF results in an increase in the amount of acid-washing aqueous alkaline waste. Therefore, in this invention, the molar ratio of the HF to the 1,1,1,3,3-pentachloropropane is controlled to be 9-15:1, preferably 9-12:1.

In the second reactor, HFO-1233zd and HCFO-1233xf perform a fluorine-chlorine exchange reaction with the HF. Temperature is a main factor that determines the reaction. If the temperature is too high, it leads to higher conversion rates of the HFO-1233zd and HCFO-1233xf, higher yields of HFO-1234ze and HFO-1234yf, and a lower yield of co-produced HFO-1233zd, and the catalyst is deactivated due to fast carbon deposition. If the temperature is too low, it leads to lower conversion rates of the HFO-1233zd and HCFO-1233xf, a larger amount of HCFO-1233xf returned back into the reactor, a higher yield of HFO-1233zd, lower yields of HFO-1234ze and HFO-1234yf. Therefore, the reaction temperature can be adjusted according to the demands of the market and products. The reaction temperature of the second reactor of this invention is selected to be 250-450° C., preferably 300-400° C.

In this invention, the main cause of deactivating the catalyst in the two-step reaction is carbon deposition, resulting in a reduction in the specific area and micropores of the catalyst. The activity of the catalyst can be recovered by a method of regeneration. At a temperature of 330-380° C., air and nitrogen gas are directed in a ratio to remove the carbon deposited on the surface of the catalyst.

The catalysts in the upper and lower sections of the first reactor of this invention are prepared by methods known in the prior art. The aluminum oxide support is immersed in a chromium solution with a certain concentration; after reaching a certain loading amount, the obtained substance is dried and calcined to obtain a catalyst precursor; and the catalyst precursor is fluorinated to obtain the catalyst for the upper section. The chromic oxide support is immersed in indium solution with a certain concentration; after reaching a certain loading amount, the obtained substance is dried and calcined to obtain the catalyst precursor; and the catalyst precursor is fluorinated to obtain the catalyst for the lower section. The catalyst used in the second reactor may be a catalyst which takes chromic oxide known in the art as the active ingredient. The catalyst is prepared using the steps: reacting nitrates of chromium, magnesium and zinc with a precipitant to generate suspended hydroxide solids; filtering, obtaining oxides of chromium, magnesium and zinc after washing, drying and calcining; obtaining the catalyst precursor by pelleting, pressing and molding; and obtaining the catalyst by fluorinating. The activation of the catalyst may proceed in other reactors.

The first reactor and the second reactor in this invention may be isothermal or heat-insulating type reactors. The material of the reactors may select a material resistant to acid corrosion, for example, Inconel.

Compared with the prior art, this invention has the following advantages:

1. Simple process: The first reactor is filled with two different types of catalysts, so that two reactions may occur at the same time to simplify the process flow.

2. High conversion rate: By adjusting the reaction temperature, the conversion rates of HCC-240fa and 1,1,2,3-tetrachloropropene may reach 100%.

3. Low energy consumption: The lower section of the first reactor is not required to be heated from the outside, and the heat required by the reaction is supplied by the material coming from the upper section to realize comprehensive heat utilization and reducing energy consumption.

4. Small investment, and high operation flexibility: A set of devices can produce three products, namely HFO-1233zd, HFO-1234yf and HFO-1234ze, and the product ratios can be flexibly adjusted according to the demands of the market, thereby obviously reducing investments in the devices.

BRIEF DESCRIPTION OF THE DRAWINGS

FIG. 1 is a process flowchart of this invention.
As shown in the FIGURE, 1—preheater; 2—first reactor; 3—second reactor; 4—hydrogen chloride tower; 5—water washing tower; 6—alkaline washing tower; 7—drying tower; 8—first rectifying tower; 9—second rectifying tower; 10—third rectifying tower; 11—21 pipelines.

DESCRIPTION OF THE EMBODIMENTS

The process flow of this invention can be seen in FIG. 1. The first reactor is divided into two sections, namely an upper section and a lower section, each filled with a different catalyst. Raw materials, hydrogen fluoride and HCC-240fa, are input in a certain molar ratio into a preheater 1 via a pipeline 11 to be preheated, and then enter the top of the upper section of a first reactor 2 via a pipeline 12. 1,1,2,3-tetrachloropropene is input into the lower section of the first reactor 2, and a mixture of HFO-1233zd, HFO-1234ze, HCFO-1233xf, hydrogen chloride and hydrogen fluoride is obtained after reaction. The mixture is directly input into a second reactor 3 via a pipeline 13 without separation. After reaction, a mixture of HFO-1234yf, HFO-1234ze, HCFO-1233xf, HFO-1233zd, hydrogen chloride and hydrogen fluoride is obtained and enters a hydrogen chloride tower 4 via a pipeline 14 to obtain a tower bottom fraction and an tower top fraction. The tower top fraction of the hydrogen chloride tower 4 is hydrogen chloride, and the hydrogen chloride is separately refined to obtain hydrochloric acid. The tower bottom fraction enters a water washing tower 5 via a pipeline 15 to be washed with water, then enters an alkaline washing tower 6 via a pipeline 16 to be washed with alkali, next enters a drying tower 7 via a pipeline 17 to be dried to obtain a mixture of HFO-1234yf, HFO-1234ze, HCFO-1233xf and HFO-1233zd. The mixture of HFO-1234yf, HFO-1234ze, HCFO-1233xf and HFO-1233zd enters a first rectifying tower 8 via a pipeline 18 to obtain a tower bottom fraction and an tower top fraction. The tower top fraction of the first rectifying tower 8 includes HFO-1234yf and HFO-1234ze, and enters a third rectifying tower 10 via a pipeline 21. A product HFO-1234yf is obtained at the top of the third rectifying tower 10, and a product HFO-1234ze is obtained in the tower bottom of the third rectifying tower 10. The tower bottom fraction of the first rectifying tower 8 enters a second rectifying tower 9 via a pipeline 19 to be separated to obtain a tower bottom fraction and an tower top faction of the second rectifying tower 9. The fraction at the top of the second rectifying tower 9 mainly includes HCFO-1233xf and carries a small amount of HFO-1233zd, and is circulated to enter the second reactor. A product HFO-1233zd is obtained in the tower bottom of the second rectifying tower 9.

This invention is described in further detail in conjunction with embodiments. However, this invention is not merely limited to the following embodiments.

Embodiment 1

First, 100 mL of $Cr_2O_3$/In catalyst (3 wt % In loading amount) is placed in the lower section of a first reactor, and 100 mL of $Al_2O_3$/Cr catalyst (10 wt % of Cr loading amount) is placed in the upper section of the first reactor. Next, 200 mL of chromium-magnesium-zinc catalyst (the catalyst includes, in mass percentage, 80% of chromic oxide, 10% of magnesium oxide, and 10% of zinc oxide) is placed into a second reactor.

Then, the first reactor is heated to a temperature of 350° C., while HF and nitrogen gas are input to perform activation for 50 hours at an HF flow rate of 100 g/h and a nitrogen flow rate of 1.5 L/min. The second reactor is heated to a temperature of 350° C., while HF and nitrogen gas are input to perform activation for 40 hours at an HF flow rate of 100 g/h and a nitrogen flow rate of 1.5 L/min. In this way, the activation of the catalysts in the two reactors is completed. The first reactor and the second reactor are heated, a temperature increase rate is 1° C./min from room temperature to 150° C., and a temperature increase rate is 0.5° C./min when the temperature is above 150° C.

Subsequently, materials are fed for reaction. The HF and HCC-240fa are input into a preheater to be preheated, where the molar ratio of the HF to HCC-240fa is 9:1. The temperature of the upper section of the first reactor is controlled to be 280° C., the air flow rate is controlled to be 500 $h^{-1}$, the molar ratio of the 1,1,2,3-tetrachloropropene to the HF is 4:9. A mixture of HFO-1233zd, a small amount of HFO-1234ze, HCFO-1233xf, hydrogen chloride and hydrogen fluoride is obtained in the first reactor. Composition of organic compounds are shown in Table 1 after gas chromatography analysis. The mixture coming from the outlet of the first reactor directly enters the second reactor, where the temperature of the second reactor is 300° C., and the air flow rate is 800 $h^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 1 after gas chromatography analysis.

TABLE 1

Composition of Organics at the reactor exit in Embodiment 1

| Reactor/fraction | HFO-1234yf | HFO-1234ze | HFO-1233zd | HCFO-1233xf | Others |
|---|---|---|---|---|---|
| First reactor (%) | 0 | 1.5 | 55 | 43.4 | 0.1 |
| Second reactor (%) | 22.5 | 28.6 | 18.5 | 30.3 | 0.1 |

Embodiment 2

First, 100 mL of $Cr_2O_3$/In catalyst (5 wt % In loading amount) is placed in the lower section of a first reactor, and 100 mL of $Al_2O_3$/Cr catalyst (15 wt % of Cr loading amount) is placed in the upper section of the first reactor. Next, 200 mL of chromium-magnesium-zinc catalyst (the catalyst includes, in mass percentage, 70% of chromic oxide, 15% of magnesium oxide, and 15% of zinc oxide) is placed into a second reactor.

The activation method of the catalysts is the same as that in Embodiment 1.

Subsequently, materials are fed for reaction. The HF and HCC-240fa are input into a preheater to be preheated, where the molar ratio of the HF to HCC-240fa is 10:1. The temperature of the upper section of the first reactor is controlled to be 300° C., the air flow rate is controlled to be 600 $h^{-1}$, the molar ratio of the 1,1,2,3-tetrachloropropene to the HF is 5:9. A mixture of HFO-1233zd, a small amount of HFO-1234ze, HCFO-1233xf, hydrogen chloride and hydrogen fluoride is obtained in the first reactor. Composition of organic compounds are shown in Table 2 after gas chromatography analysis. The mixture coming from the outlet of the first reactor directly enters the second reactor, where the temperature of the second reactor is 320° C., and the air flow rate is 800 $h^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 2 after gas chromatography analysis.

TABLE 2

Composition of Organics at the reactor exit in Embodiment 2

| Reactor/fraction | HFO-1234yf | HFO-1234ze | HFO-1233zd | HCFO-1233xf | Others |
|---|---|---|---|---|---|
| First reactor (%) | 0 | 1.8 | 46.9 | 51.2 | 0.1 |
| Second reactor (%) | 25.8 | 31.6 | 17.1 | 25.3 | 0.2 |

Embodiment 3

First, 100 mL of $Cr_2O_3$/In catalyst (10 wt % In loading amount) is placed in the lower section of a first reactor, and 100 mL of $Al_2O_3$/Cr catalyst (5 wt % of Cr loading amount) is placed in the upper section of the first reactor. Next, 200 mL of chromium-magnesium-zinc catalyst (the catalyst includes, in mass percentage, 80% of chromic oxide, 12% of magnesium oxide, and 8% of zinc oxide) is placed into a second reactor.

The activation method of the catalysts is the same as that in Embodiment 1.

Subsequently, materials are fed for reaction. The HF and HCC-240fa are input into a preheater to be preheated, where the molar ratio of the HF to HCC-240fa is 15:1. The temperature of the upper section of the first reactor is controlled to be 320° C., the air flow rate is controlled to be 1000 h$^{-1}$, the molar ratio of the 1,1,2,3-tetrachloropropene to the HF is 3:9. A mixture of HFO-1233zd, a small amount of HFO-1234ze, HCFO-1233xf, hydrogen chloride and hydrogen fluoride is obtained in the first reactor. Composition of organic compounds are shown in Table 3 after gas chromatography analysis. The mixture coming from the outlet of the first reactor directly enters the second reactor, where the temperature of the second reactor is 350° C., and the air flow rate is 1200 h$^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 3 after gas chromatography analysis.

TABLE 3

Composition of Organics at the reactor exit in Embodiment 3

| Reactor/fraction | HFO-1234yf | HFO-1234ze | HFO-1233zd | HCFO-1233xf | Others |
|---|---|---|---|---|---|
| First reactor (%) | 0 | 2.7 | 38.6 | 58.5 | 0.2 |
| Second reactor (%) | 31.3 | 29.4 | 16.6 | 22.6 | 0.1 |

Embodiment 4

First, 100 mL of Cr$_2$O$_3$/In catalyst (8 wt % In loading amount) is placed in the lower section of a first reactor, and 100 mL of Al$_2$O$_3$/Cr catalyst (8 wt % of Cr loading amount) is placed in the upper section of the first reactor. Next, 200 mL of chromium-magnesium-zinc catalyst (the catalyst includes, in mass percentage, 80% of chromic oxide, 15% of magnesium oxide, and 5% of zinc oxide) is placed into a second reactor.

The activation method of the catalysts is the same as that in Embodiment 1.

Subsequently, materials are fed for reaction. The HF and HCC-240fa are input into a preheater to be preheated, where the molar ratio of the HF to HCC-240fa is 12:1. The temperature of the upper section of the first reactor is controlled to be 400° C., the air flow rate is controlled to be 300 h$^{-1}$, the molar ratio of the 1,1,2,3-tetrachloropropene to the HF is 4:9. A mixture of HFO-1233zd, a small amount of HFO-1234ze, HCFO-1233xf, hydrogen chloride and hydrogen fluoride is obtained in the first reactor. Composition of organic compounds are shown in Table 4 after gas chromatography analysis. The mixture coming from the outlet of the first reactor directly enters the second reactor, where the temperature of the second reactor is 400° C., and the air flow rate is 500 h$^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 4 after gas chromatography analysis.

TABLE 4

Composition of Organics at the reactor exit in Embodiment 4

| Reactor/fraction | HFO-1234yf | HFO-1234ze | HFO-1233zd | HCFO-1233xf | Others |
|---|---|---|---|---|---|
| First reactor (%) | 0 | 3.1 | 44.5 | 52.3 | 0.1 |
| Second reactor (%) | 28.6 | 25.3 | 18.2 | 27.8 | 0.1 |

Embodiment 5

First, 100 mL of Cr$_2$O$_3$/In catalyst (6 wt % In loading amount) is placed in the lower section of a first reactor, and 100 mL of Al$_2$O$_3$/Cr catalyst (10 wt % of Cr loading amount) is placed in the upper section of the first reactor. Next, 200 mL of chromium-magnesium-zinc catalyst (the catalyst includes, in mass percentage, 80% of chromic oxide, 10% of magnesium oxide, and 10% of zinc oxide) is placed into a second reactor.

The activation method of the catalysts is the same as that in Embodiment 1.

Subsequently, materials are fed for reaction. The HF and HCC-240fa are input into a preheater to be preheated, where the molar ratio of the HF to HCC-240fa is 10:1. The temperature of the upper section of the first reactor is controlled to be 300° C., the air flow rate is controlled to be 500 h$^{-1}$, the molar ratio of the 1,1,2,3-tetrachloropropene to the HF is 4:9. A mixture of HFO-1233zd, a small amount of HFO-1234ze, HCFO-1233xf, hydrogen chloride and hydrogen fluoride is obtained in the first reactor. Composition of organic compounds are shown in Table 5 after gas chromatography analysis. The mixture coming from the outlet of the first reactor directly enters the second reactor, where the temperature of the second reactor is 330° C., and the air flow rate is 600h$^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 5 after gas chromatography analysis.

TABLE 5

Composition of Organics at the reactor exit in Embodiment 5

| Reactor/fraction | HFO-1234yf | HFO-1234ze | HFO-1233zd | HCFO-1233xf | Others |
|---|---|---|---|---|---|
| First reactor (%) | 0 | 1.0 | 52.8 | 46.1 | 0.1 |
| Second reactor (%) | 15.3 | 22.5 | 31.2 | 31 | 0 |

Embodiment 6

First, 100 mL of Cr$_2$O$_3$/In catalyst (8 wt % In loading amount) is placed in the lower section of a first reactor, and 100 mL of Al$_2$O$_3$/Cr catalyst (10 wt % of Cr loading amount) is placed in the upper section of the first reactor. Next, 200 mL of chromium-magnesium-zinc catalyst (the catalyst includes, in mass percentage, 75% of chromic oxide, 15% of magnesium oxide, and 10% of zinc oxide) is placed into a second reactor.

The activation method of the catalysts is the same as that in Embodiment 1.

Subsequently, materials are fed for reaction. The HF and HCC-240fa are input into a preheater to be preheated, where the molar ratio of the HF to HCC-240fa is 9:1. The temperature of the upper section of the first reactor is controlled to be 300° C., the air flow rate is controlled to be 600 h$^{-1}$, the molar ratio of the 1,1,2,3-tetrachloropropene to the HF is 4:9. A mixture of HFO-1233zd, a small amount of HFO-1234ze, HCFO-1233xf, hydrogen chloride and hydrogen fluoride is obtained in the first reactor. Composition of organic compounds are shown in Table 6 after gas chromatography analysis. The mixture coming from the outlet of the first reactor directly enters the second reactor, where the temperature of the second reactor is 300° C., and the air flow rate is 700 h$^{-1}$. After a reaction, a mixture of HFO-1234yf, HFO-1234ze, HCFO-1233xf, HFO-1233zd, hydrogen chloride and hydrogen fluoride is obtained. Composition of organic compounds are shown in Table 6 after gas chromatography analysis.

TABLE 6

Composition of Organics at the reactor exit in Embodiment 6

| Reactor/fraction | HFO-1234yf | HFO-1234ze | HFO-1233zd | HCFO-1233xf | Others |
|---|---|---|---|---|---|
| First reactor (%) | 0 | 1.2 | 48.5 | 50.2 | 0.1 |
| Second reactor (%) | 20.1 | 25.3 | 20.4 | 34 | 0.2 |

What is claimed is:

1. A method for co-production of 1-chloro-3,3,3-trifluoropropene, 2,3,3,3-tetrafluoropropene and 1,3,3,3-tetrafluoropropene, the method comprising:
   (a) preheating and then directing hydrogen fluoride and 1,1,1,3,3-pentachloropropane into a first reactor in a molar ratio of 9:1-15:1, wherein the first reactor comprises an upper section filled with an aluminum oxide supported chromium metal catalyst and a lower section filled with a chromic oxide supported indium metal catalyst, wherein the hydrogen fluoride and the 1,1,1,3,3-pentachloropropane are reacted in the upper section of the first reactor at a temperature of 200-400° C. and at an air flow rate of 300-1,000 h$^{-1}$, and a product from the upper section enters the lower section of the first reactor to continuously react with the 1,1,2,3-tetrachloropropane to obtain a first reaction product of the first reactor, wherein a molar ratio of the 1,1,2,3-tetrachloropropane to the hydrogen fluoride in the lower section of the first reactor is 3:9-5:9;
   (b) directly directing the first reaction product of the first reactor into a second reactor to perform a reaction catalysed by a catalyst at a temperature of 250-450° C. and at an air flow rate of 500-1,500 h$^{-1}$ to obtain a second reaction product of the second reactor;
   (c) separating the second reaction product of the second reactor in a hydrogen chloride tower to obtain a first tower bottom fraction and a first tower top fraction, which is hydrogen chloride that is refined to obtain hydrochloric acid;
   (d) removing hydrogen fluoride and hydrogen chloride from the first tower bottom fraction of the hydrogen chloride tower by sequentially passing the first tower bottom fraction through a water washing tower, an alkaline washing tower and a drying tower to obtain a substance;
   (e) directing the substance into a first rectifying tower to obtain a second tower bottom fraction and a second tower top fraction;
   (f) directing the second tower bottom fraction of the first rectifying tower into a second rectifying tower to obtain 1-chloro-3,3,3-trifluoropropene and a third tower top fraction; and
   (g) directing the second tower top fraction of the first rectifying tower into a third rectifying tower to obtain 2,3,3,3-tetrafluoropropene at the top of the third rectifying tower and 1,3,3,3-tetrafluoropropene at the bottom of the third rectifying tower.

2. The method of claim 1, further comprising circulating the third top fraction from the second rectifying tower to the second reactor.

3. The method of claim 1, wherein the molar ratio is 9:1-12:1, the temperature is 250-320° C. and the air flow rate is 500-800 h$^{-1}$ for the hydrogen fluoride and the 1,1,1,3,3-pentachloropropane reacted in step (a).

4. The method of claim 1, wherein the temperature is 300-400° C. and the air flow rate is 800-1,200 h$^{-1}$ for the reaction in step (b).

5. The method of claim 1, wherein the loading amount of chromium in the aluminum oxide supported chromium metal catalyst is 5-15 wt % in step (a).

6. The method of claim 1, wherein the loading amount of indium in the aluminum oxide supported indium metal catalyst is 3-10 wt % in step (a).

7. The method of claim 1, wherein the catalyst in the second reactor comprises 70-80 wt % of chromium oxide, 10-15 wt % of magnesium oxide, and 5-15 wt % of zinc oxide.

* * * * *